US006471965B1

(12) United States Patent
Golubev et al.

(10) Patent No.: US 6,471,965 B1
(45) Date of Patent: *Oct. 29, 2002

(54) VACCINE CONTAINING WHOLE KILLED HERPES VIRUSES TO PREVENT DEVELOPMENT OF ATHEROSCLEROTIC PLAQUE

(75) Inventors: Daniel Golubev, New York, NY (US); Alexander Chaihorsky, Garfield, NJ (US)

(73) Assignee: Bio-Virus Research Incorporated, San Matteo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/281,703

(22) Filed: Jul. 27, 1994

(51) Int. Cl.$^7$ .......................... A61K 39/27; C12N 7/06
(52) U.S. Cl. ................... 424/229.1; 424/204.1; 424/230.1; 424/231.1; 514/824; 435/5; 435/238
(58) Field of Search .............. 424/230.1, 231.1, 424/204.1, 229.1; 514/824; 435/238, 5

(56) References Cited

U.S. PATENT DOCUMENTS

| 4,038,381 A | | 7/1977 | Perlant | |
|---|---|---|---|---|
| 4,322,404 A | * | 3/1982 | Gauri et al. | 424/89 |
| 4,693,981 A | * | 9/1987 | Wiesehahn et al. | 435/238 |

FOREIGN PATENT DOCUMENTS

| WO | WO 94/03207 | * | 2/1994 |
|---|---|---|---|

OTHER PUBLICATIONS

Dundarov et al. Develop. Biol. Standard. vol. 52:351–358, 1982.*
Gonzales ER JAMA 243(11): 1128 & 1130, Mar. 1980.*
Fabricant et al. "Vaccination Prevents Atherosclerosis Induced by Marek's Disease Herpes Viruses", College of Veterinary Medicine & Medicine, Cornell University, Ithaca, New York, N.Y. In: the Federation of American Societies for Exp. Medicine. 65th Annual Matiny Atlanta, abstract 583, p. 335.*
Roizman, B. (1991) Reviews of Infectious Diseases vol. 13, Suppl. 11, pp 5892–5894.*
Hajjar, D.P. (1991) Am. J. Pathology vol. 139, pp 1195–1211.*
IXth International Congress of Virology, Glasgow, Scotland, Aug. 8–13, 1993, "Herpesviruses" p. 32.
Vercellotti, G., Trends in Cardiovascular Medicine, vol. 5, No. 4, 128–133, Jul. /Aug. 1995.*
Hajjar, D., J. Clin. Invest., vol. 80, 1317–1321, Nov., 1987.*

* cited by examiner

Primary Examiner—Mary K. Zeman
(74) Attorney, Agent, or Firm—Herbert Dubno; Jonathan Myers

(57) ABSTRACT

A vaccine is disclosed for the prophylaxis against pathogenic development of atherosclerotic plaque in a mammalian subject susceptible thereto which consists essentially of a multiplicity of killed whole-virus strains, selected from the group consisting of:

Herpes Simplex Virus 1;
Herpes Simplex Virus 2;
Herpes Simplex Virus 6;
Human Cytomegalovirus; and
Epstein-Barr Virus;

in combination with a pharmaceutically acceptable inert vaccine carrier or diluent.

2 Claims, No Drawings

VACCINE CONTAINING WHOLE KILLED HERPES VIRUSES TO PREVENT DEVELOPMENT OF ATHEROSCLEROTIC PLAQUE

FIELD OF THE INVENTION

This invention relates to a vaccine containing herpes virus for the prevention of atherosclerosis. More particularly the invention relates to a herpes vaccine containing several types of whole killed herpes viruses that affect humans and that acts as a prophylaxis against pathogenic development of atherosclerotic plaque in a mammalian subjected susceptible thereto.

BACKGROUND OF THE INVENTION

It is generally accepted that atherogenesis is triggered by primary injury to the endothelial lining of the arterial walls. This injury is believed to be the result of exposure of the underlying smooth muscle tells to several factors of non-infectious origin (hormones, low density lipoproteins, growth factors, among others). The prevailing view is that human atherosclerosis (AS) is a pleiotropic process with various causes. See Ross, R., The Pathogenesis of Atherosclerosis: An Update, New England J. Med.,314, 488 to 500 (1986).

A fundamentally new etiological factor: herpes virus infection-was reported by Fabricant et al, who demonstrated that chickens infected with Marek Disease Virus (MDV), have an unusually high incidence of atherosclerotic plaque- (ASP) in the arteries. See Fabricant, C. G. et al, Virus-Induced Cholesterol Crystals, Science, 181, 566 to 567 (1973); and Fabricant, C. G. et al, Virus-Induced Atherosclerosis, J. Exp. Med., 148, 335 to 340 (1978). Since that time data have been accumulated suggesting the role of herpes virus in AS in humans. It was shown that different herpes viruses can alter smooth muscle cells lipid metabolism and induce cholesterol and cholesterol ester accumulation in these cells. See Fabricant, C. G. et al, Herpes Virus Infection Enhances Cholesterol and Cholesterol Ester Accumulation in Cultured Arterial Smooth Muscle Cells, Am. J. Pathol, 105, 176 to 184 (1981); Fabricant, C. G. et al, Herpes Virus-Induced Atherosclerosis in Chickens, Fed. Proc., 42, 2476 to 2479 (1983); Melnick, J. L. et al, Cytomegalovirus Antigen within Human Arterial Smooth Muscle Cells, Lancet, ii, 644 to 647 (1983); Gyorkey, F. et al, Herpesviridae in the Endothelial and Smooth Muscle Cells of Proximal Aorta in Atherosclerotic Patients, Exp. Mol. Pathol, 40, 328 to 339 (1984); Hajjar et al, Virus-Induced Atherosclerosis: Herpes Virus Infection Alters Aortic Cholesterol Metabolism and Accumulation, Am. J. Pathol., 122, 62 to 70 (1986); Adam et al, High Levels of Cytomegalovirus Antibody in Patients Requiring Vascular Surgery for Atherosclerosis, Lancet, 2, 291 to 293 (1987); Petrie, Association of Herpesvirus/Cytomegalovirus Infections with Human Atherosclerosis, Prog. Med. Virol., 35, 21 to 42 (1988); Grattan, M. T. et al, Cytomegalovirus Infection is Associated with Cardiac Allograft Rejection and Atherosclerosis, J. A. Med. Assoc., 261, 3561 to 3566 (1989); Mc Donald, K. et al, Association of Coronary Artery Disease in Cardiac Transplant Recipients with Cytomegalovirus Infection, Am. J. Cardiol., 64, 359 to 362 (1989); Visser et al, Granulocyte-Mediated Injury in Herpes Simplex Virus-Infected Human Endothelium, Lab. Invest., 60, 296 to 304 (1989); Melnick, J. L. et al, Possible Role of Cytomegalovirus in Atherogenesis, J. Am. Assoc., 263, 2204 to 2207 (1990); Bruggeman, C. A. et al, The Possible Role of Cytomegalovirus in Atherogenesis, Prog. Med. Virol., 38, 1 to 26 (1991); Melnick, J. L. et al, Accelerated Graft Atherosclerosis Following Cardiac Transplantation; Do Viruses Play a Role?, Clin. Cardiol., 14 (Supp. II), 21 to 26 (1991); and Hajjar , D. P., Viral Pathogenesis of Atherosclerosis, Am. J. Pathol., 133, 1195 to 1211 (1991).

In addition the DNA of various herpes viruses showed positive hybridization with ASP DNA; see Benditt, E. P. et al, Viruses in the Etiology of Atherosclerosis, Proc. Natl. Acad. Sci., 80, 6386 to 6389 (1983); Pyrzak, R. et al, Detection of Specific DNA Segments of Marek's Disease Herpes Virus in Japanese Quail Susceptible to Atherosclerosis, Atherosclerosis, 68, 77 to 85 (1987); Petrie, B. L. et al, Nucleic Acid Sequences of Cytomegalovirus in Cultured Human Arterial Tissue, J. Inf. Dis., 155, 158 to 159 (1987); Yamashiroya, H. M. et al, Herpesviridae in Coronary Arteries and Aorta of Young Trauma Victims, Am. J. Pathol, 130, 71 to 79 (1988); and Hendrix, M. G. R. et al, The Presence of Cytomegalovirus Nucleic Acids in Arterial Walls of Patients Suffering From Grade III Atherosclerosis, Am. J. Pathol., 134, 1151 to 1157 (1989).

No systematic attempts to demonstrate a viral presence in ASP by direct isolation of infectious HSV from ASP and by detection of viral replication in ASP by Electron Microscopy have been reported. A viral presence in ASP would explain the presence of HSV-like DNA in ASP, and redirect research to determine the molecular mechanisms of viral involvement in etiology of atherosclerosis. In such a case, the possibility of a contamination of ASP in the blood vessels by HSV also has to be excluded.

None of the above references deals with the preparation of a vaccine against any form of the herpes virus infection. The following reference deals with the preparation of a herpes vaccine against Marek's Disease Herpes-Virus in chickens: Fabricant, J. et al, Vaccination Prevents Atherosclerosis Induced by Marek's disease Herpesvirus, College of Veterinary Medicine and Medicine, Cornell University, Ithaca and New York, N.Y. The reference appeared as an abstract in the Federation of American Societies for Experimental Biology, 65th Annual Meeting, Atlanta (1981).

The vaccine employed against Marek's Disease Herpesvirus in chickens was derived from Turkey herpesvirus (HVT). There is no indication that a vaccine against atherosclerosis caused by human herpes virus could be prepared. There is no suggestion to employ a herpes vaccine containing whole killed viruses from many different types of herpes with the ability to serve as a prophylaxis to the pathogenic development of atherosclerotic plaque.

U.S. Pat. No. 4,038,381 is directed to a vaccine for the prevention and treatment of vascular conditions, comprising a combination of a tuberculosis antigen with an antiherpes vaccine. The reference indicates that neither component per se of the vaccine had any known utility in the prevention or treatment of vascular disease. Nor is there any suggestion in the reference to prepare a herpes vaccine containing whole killed viruses from many different types with the ability to serve as a prophylaxis to the pathogenic development of atherosclerotic plaque.

OBJECT OF THE INVENTION

It is the object of the invention to provide a vaccine as a prophylaxis against pathogenic development of atherosclerotic plaque in a mammalian subject susceptible thereto.

SUMMARY OF THE INVENTION

We have discovered such a vaccine effective as a prophylaxis in a mammalian subject, including man, against the pathogenic development of human atherosclerotic plaque. The vaccine comprises a mixture of inactivated whole viruses of the following strains:

Herpes Simplex Virus 1;

Herpes Simplex Virus 2;

Herpes Simplex Virus 6;

Human Cytomegalovirus; and

Epstein-Barr Virus;

in combination with a pharmaceutically acceptable inert vaccine carrier such as normal saline or a physiological oil in an adequate concentration of said inactivated whole viruses. Preferably there is present 15 µg per of each whole killed virus per ml of pharmaceutical composition. Thus the total amount of pure viruses in one dose of vaccine is 75 µg.

Each of the five abovementioned whole killed viruses is preferably. present in the compositions in an amount of 15 to 25% by either weight or volume. More preferably equal amounts of each of the whole killed virus are present, that is the compositions contain about 20% by weight or volume of each of the five whole killed viruses as active ingredient.

Also contemplated to be within the scope of the invention is a method of prophylaxis of pathogenic development of atherosclerotic plaque in a mammalian subject susceptible thereto which comprises the step of administering to said mammalian subject, a therapeutically effective amount of the pharmaceutical composition containing the whole killed herpes viruses as described hereinabove.

The pharmaceutical composition may preferably be administered to a mammalian subject parenterally, such as by injection. More preferably the compositions are administered by subcutaneous, intramuscular, intra-arterial, intravenous, or intradermal injection. A preferred dosage of the composition is 1 ml every 20 days administered as a series of 6 intramuscular injections. The full cycle of treatment may consist of 2 or 3 such courses with 3 month intervals in between.

Use of an adjuvant, for instance inorganic gels such as alum, aluminum hydroxide or aluminum phosphate that increase antigenic response, is optional in the compositions.

Preparation of the Whole Killed Virus Vaccine

The Herpes Simplex Viruses 1 and 2 and the Human Cytomegalovirus are cultivated in several strains of diploid human lung cells. The final concentration of viruses in a culture fluid, not less than one million PFU (plaque forming units) per 0.1 ml.

Herpes Simplex Virus 6 and Epstein-Barr Virus are cultivated in a suspension of human lymphocytes. The final concentration is not less than 100,000 TCD (tissue cytopathic doses).

The virus suspensions are purified and concentrated by centrifugation and then inactivated either by formaldehyde or ultraviolet radiation. The inactivated virus concentrates are then added to the pharmaceutically acceptable inert viral carrier such as normal saline or a physiological oil to obtain the vaccine.

Tissue Cultures. Viruses.

Tissue cultures

For cultivation of Herpes Simplex Virus 1 and 2 and Human Cytomegalovirus it is necessary to use diploid human embryonic lung cells (HECL), e.g. semi-continuous cell. These cells are derived from embryonic lung tissue and, following initial dispersal, they can be redispersed and regrown many times (usually 30 to 50 passages). Human embryo lung tissue, which is obtained from embryos of 10–12 weeks, provide a most valuable source for harvesting different herpesviruses, including Herpes Simplex Viruses and Human Cytomegalovirus.

Semi-continuous cells have a normal chromosome count (diploid) and show the phenomenon of contact inhibition.

The inoculum of each viruses listed above is placed on the monolayer and allowed to adsorb (1 hour). It is then removed and fresh medium is added. Cultures are incubated at 37° C. and they are inspected regularly by microscopy for evidence of virus growth. The culture medium is normally changed on the day after inoculation to minimize the effect of toxins that may present in the inoculum, and is then replaced periodically to replenish the supply of nutrients for the cells. Cultures are incubated for varying lengths of time depending on the virus. While the cytopathic effects of a heavy inoculum of herpes virus may appear overnight, a low level of cytomegalovirus may take 3–4 weeks to appear.

These cells infected by herpesviruses may be cultivated in suspension also.

For cultivation of Burkitt's lymphoma (Epstein-Barr virus) and Herpesvirus 6 it is necessary to use the primary human lymphocytes culture in suspension. For its preparation it is necessary to obtain the peripheral donor's blood and then to separate red blood cells from plasma. For this aim heparin (250 ed./ml) is added to the blood and after exposition at moderate T the red cells subside. Plasma has to be transformed by centrifugation in the ficols gradient for receiving the special "lymphocyte's" zone. This zone has to be separated, washed by Eagle's medium and then cultivated with RPM 16–40 medium inn suspension. EBV is added after 24 hours.

Viruses.

For inoculation of tissue cultures during preparing the whole vaccines the following viral strains are preferably used:

Herpes simplex type 1 (Human herpesvirus 1; Herpesvirus hominis type 1) ATCC VR-539. Strain: MacIntyre.

Herpes simplex type 2 (Human herpesvirus 2; Herpesvirus hominis type 2) ATCC VR-540. Strain: MS.

Cytomegalovirus (Human Cytomegalovirus) ATCC VR-538. Strain: AD-169.

Burkitt lymphoma (Epstein-Barr virus)-ATCCR VR-602. Strain: P-3 and

Herpesvirus type 6-strain Z-29, Prize code: Q P-1348.

What is claimed is:

1. A killed whole-virus vaccine pharmaceutical composition for preventing pathogenic development of atherosclerotic plaque, which consists essentially of the following strains in an amount effective to prevent atherosclerotic plaque development:

Herpes Simplex Virus 1;

Herpes Simplex Virus 2;

Herpes Simplex Virus 6;

Human Cytomegalovirus; and

Epstein-Barr Virus;

in combination with a pharmaceutically acceptable inert vaccine carrier or diluent.

2. A method of preventing pathogenic development of atherosclerotic plaque in a mammalian subject susceptible thereto, comprising the step of administering to said mammalian subject, a therapeutically effective amount of a killed whole-virus vaccine pharmaceutical composition which consists essentially of the following strains:

Herpes Simplex Virus 1;

Herpes Simplex Virus 2;

Herpes Simplex Virus 6;

Human Cytomegalovirus; and

Epstein-Barr Virus;

in combination with a pharmaceutically acceptable inert vaccine carrier or diluent.

* * * * *